(12) United States Patent
Miller et al.

(10) Patent No.: US 9,919,008 B2
(45) Date of Patent: *Mar. 20, 2018

(54) METHOD FOR TREATING AGE-RELATED HEARING LOSS (ARHL)

(71) Applicants: The Regents of the University of Michigan, Ann Arbor, MI (US); Universidad de Castilla-La Mancha, Instituto de Investigación en Discapacidades Neurológicas-IDINE, Albacete (ES)

(72) Inventors: Josef M. Miller, Ann Arbor, MI (US); José M. Juiz Gómez, Albacete (ES); Juan C. Alvarado-Romero, Albacete (ES); Verónica Fuentes-Santamaría, Albacete (ES)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/272,981

(22) Filed: Sep. 22, 2016

(65) Prior Publication Data

US 2017/0065632 A1    Mar. 9, 2017

Related U.S. Application Data

(63) Continuation-in-part of application No. 14/847,178, filed on Sep. 8, 2015, now Pat. No. 9,770,433, which is a continuation-in-part of application No. 13/839,760, filed on Mar. 15, 2013, now Pat. No. 9,144,565, which is a continuation-in-part of application No. 13/679,224, filed on Nov. 16, 2012, now Pat. No. 8,927,528, which is a continuation-in-part of application No. 12/761,121, filed on Apr. 15, 2010, now Pat. No. 8,338,397, which is a continuation-in-part of application No. 11/623,888, filed on Jan. 17, 2007, now Pat. No. 7,951,845, said application No. 13/679,224 is a continuation-in-part of application No. 13/091,931, filed on Apr. 21, 2011, now Pat. No. 8,338,398, which is a continuation of application No. 11/623,888, filed on Jan. 17, 2007, now Pat. No. 7,951,845.

(60) Provisional application No. 60/760,055, filed on Jan. 19, 2006.

(51) Int. Cl.
| | |
|---|---|
| *A61K 33/06* | (2006.01) |
| *A61K 31/355* | (2006.01) |
| *A61K 31/60* | (2006.01) |
| *A61K 31/07* | (2006.01) |
| *A61K 31/375* | (2006.01) |
| *A61K 31/245* | (2006.01) |
| *A61K 31/58* | (2006.01) |
| *A61K 31/05* | (2006.01) |
| *A61K 45/06* | (2006.01) |
| *A61K 31/341* | (2006.01) |
| *A61K 31/585* | (2006.01) |
| *A61K 33/00* | (2006.01) |
| *A61K 9/00* | (2006.01) |

(52) U.S. Cl.
CPC ............ *A61K 33/06* (2013.01); *A61K 9/0056* (2013.01); *A61K 31/05* (2013.01); *A61K 31/07* (2013.01); *A61K 31/341* (2013.01); *A61K 31/355* (2013.01); *A61K 31/375* (2013.01); *A61K 31/58* (2013.01); *A61K 31/585* (2013.01); *A61K 33/00* (2013.01); *A61K 45/06* (2013.01)

(58) Field of Classification Search
CPC ...... A61K 33/06; A61K 31/355; A61K 31/60; A61K 31/07; A61K 31/375; A61K 31/245
See application file for complete search history.

(56) References Cited

U.S. PATENT DOCUMENTS

| | | |
|---|---|---|
| 5,597,585 A | 1/1997 | Williams et al. |
| 6,093,417 A | 7/2000 | Petrus |
| 6,177,434 B1 | 1/2001 | Kopke et al. |
| 6,265,386 B1 | 7/2001 | Campbell |
| 6,288,106 B1 | 9/2001 | Pearson et al. |
| 6,423,321 B2 | 7/2002 | Tobinick |
| 6,524,619 B2 | 2/2003 | Pearson et al. |
| 6,562,378 B1 | 5/2003 | Chandra |
| 6,649,621 B2 | 11/2003 | Kopke et al. |
| 6,660,297 B2 | 12/2003 | Bartels et al. |
| 6,815,434 B2 | 11/2004 | Kil et al. |

(Continued)

FOREIGN PATENT DOCUMENTS

| | | |
|---|---|---|
| EP | 1 258 243 A1 | 11/2002 |
| WO | WO 98/56761 A2 | 12/1998 |

(Continued)

OTHER PUBLICATIONS

Abstract of Aarnisalo et al., "Apoptosis in Auditory Brainstem Neurons after a Severe Noise Trauma of the Organ of Corti: Intracochlear GDNF treatment Reduces the Number of Apoptotic Cells", ORL Original Paper, Apr. 2, 2000, No. 62, 1 page.

Abaamrane et al., "Long-term Administration of Magnesium After Acoustic Trauma Caused by Gunshot Noise in Guinea Pigs", Hearing Research 247, 2009, pp. 137-145.

Agarwal et al., "Phospholipase Activation Triggers Apoptosis in Photosensitized Mouse Lymphoma Cells", Cancer Research 53, Dec. 15, 1993, pp. 5897-5902.

Ahn et al., Anti-Apoptotic Role of Retinoic Acid in the Inner Ear of Noise-Exposed Mice, Biochemical and Biophysical Research Commmunications 335, 2005, pp. 485-490.

(Continued)

*Primary Examiner* — Sahar Javanmard
(74) *Attorney, Agent, or Firm* — Howard & Howard Attorneys PLLC (57) ABSTRACT

A method for treating age-related hearing loss (ARHL) includes the step administering a composition to the mammal, wherein the composition consists essentially of a biologically effective amount of vitamin A, vitamin E, vitamin C, a vasodilator comprising magnesium, and, optionally, a withanolide, and/or resveratrol.

20 Claims, 3 Drawing Sheets

(56) References Cited

U.S. PATENT DOCUMENTS

| | | |
|---|---|---|
| 7,786,100 B2 | 8/2010 | Miller et al. |
| 7,951,845 B2 | 5/2011 | Miller et al. |
| 8,053,424 B2 | 11/2011 | Miller et al. |
| 8,338,397 B2 | 12/2012 | Miller |
| 8,338,398 B2 | 12/2012 | Miller et al. |
| 9,144,565 B2 | 9/2015 | Miller et al. |
| 2002/0061870 A1 | 5/2002 | Pearson et al. |
| 2003/0191064 A1 | 10/2003 | Kopke |
| 2004/0033273 A1 | 2/2004 | Patwardhan et al. |
| 2004/0096524 A1 | 5/2004 | Nair et al. |
| 2004/0101560 A1 | 5/2004 | Sawchuk et al. |
| 2004/0224012 A1 | 11/2004 | Suvanprakorn et al. |
| 2004/0247570 A1 | 12/2004 | Miller et al. |
| 2004/0258781 A1 | 12/2004 | Nair et al. |
| 2005/0013854 A1 | 1/2005 | Mannino et al. |
| 2005/0070607 A1 | 3/2005 | Andrus et al. |
| 2005/0107338 A1 | 5/2005 | Seidman |
| 2015/0374659 A1 | 12/2015 | Miller et al. |

FOREIGN PATENT DOCUMENTS

| | | |
|---|---|---|
| WO | WO 01/84961 A2 | 11/2001 |
| WO | WO 03/030818 A2 | 4/2003 |
| WO | WO 2004/000297 A1 | 12/2003 |
| WO | WO 2004/016100 A2 | 2/2004 |
| WO | WO 2004/037205 A2 | 5/2004 |
| WO | WO 2004/050021 A2 | 6/2004 |

OTHER PUBLICATIONS

Altura et al., "Noise-induced hypertension and magnesium in rats: relationship to microcirculation and calcium", J Appl Physiol, 1992, 72, pp. 194-202.

Altura et al., Role of Mg ions in contractility of blood vessels and skeletal muscles. Magnesium-B 1a, 1981, pp. 102-114.

Ames et al., "Oxidants, antioxidants, and the degenerative diseases of aging", Proc. Natl. Acad. Sci. USA, Sep. 1993, vol. 90, pp. 7915-7922.

Aoshiba et al., "Acute cigarette smoke exposure induces apoptosis of alveolar macrophages", Am J Physiol Lung Cell Mol Physiol 281, 2001, pp. L1392-L1401.

Attias et al, Oral magnesium intake reduces permanent hearing loss induced by noise exposure. Am. J. Otolaryngol. 15, 2004, pp. 26-32.

Attias et al.,"Preventing noise induced otoacoustic emission loss by increasing magnesium (Mg2+) intake in guinea-pigs." J. Basic Clin. Physiol. Pharmacol. 14, 2003, pp. 119-136.

Attias et al., "Reduction in Noise-Induced Temporary Threshold Shift in Humans Following Oral Magnesium Intake", Clinical Otolaryngology 29, Blackwell Publishing Ltd, 2004, pp. 635-641.

Balavoine et al., "Peroxynitrite scavenging by different antioxidants. Part I: Convenient Assay", Nitric Oxide 3, 1999, pp. 40-54.

Bednarczyk et al., "New Properties of mitochondrial ATP-regulated potassium channels", J. Bionerg Biomembr, 2008, 40, pp. 325-335.

Bertolaso et al., "Apoptosis in the OC-k3 immortalized cell line treated with different agents", Audiology 40, 2001, pp. 327-335.

Biesalski, et al., "Vitamin A deficiency increases noise susceptibility in guinea pigs", J. Nutr. 120, 1990, pp. 726-737.

Bock et al., "Effects of N-acetylcysteine on kanamycin ototoxicity in the guinea pig", Hear Res 9, 1983, pp. 255-262.

Boland et al., "Pre- and post-treatment with pirlindole and dehydropirlindole protects cultured brain cells against nitric oxide-induced death", Eur J Pharmacol 466, 2003, pp. 21-30.

Branis et al., "Effect of Ascorbic Acid on the Numerical Hair Cell Loss in Noise Exposed Guinea Pigs", Hearing Research 33, Elsevier Science Publishers B.V., 1988, pp. 137-140.

Budinger et al., "Hyperoxia-induced Apoptosis Does Not Require Mitochondrial Reactive Oxygen Species and Is Regulated by Bcl-2 Proteins", The Journal of Biological Chemistry, vol. 277, No. 18, May 3, 2002, pp. 15654-15660.

Burton et al., "Is Vitamin E the Only Lipid-Soluble, Chain-Breaking Antioxidant in Human Blood Plasma and Erythrocyte Membranes?", Archives of Biochemistry and Biophysics, vol. 221, No. 1, Feb. 15, 1983, pp. 281-290.

Carnevali et al., "Cigarette smoke extract induced oxidative stress and apoptosis in human lung fibroblasts", Am J Physiol Lung Cell Mol Physiol 284, 2003, pp. L955-L963.

Cevette et al., "Magnesium and hearing", J. Am. Acad. Audiol. 14, 2003, pp. 202-212.

Chae et al., "Salicylate regulates COX-2 expression through ERK and subsequent NF-kappaB activation in osteoblasts", Immunopharmacol Immunotoxicol 26, 2004, pp. 75-91.

Chan et al., "Connexin-26-associated deafness: phenotypic variability and progression of hearing loss", Genet Med. 2010,12, pp. 174-181.

Cohen-Salmon et al., "Targeting Ablation of Connexin26 in the Inner Ear Epithelial Gap Junction Network Causes Hearing Impairment and Cell Death", Current Biology, vol. 12, Jul. 9, 2002, pp. 1106-1111.

Coyle et al., "Pendred syndrome (goitre and sensorineural hearing loss) maps to chromosome 7 in the region containing the nonsyndromic deafness gene DFNB4", Apr. 1996, Nature Genetics, vol. 12, pp. 421-423.

Cryns et al., "A genotype-phenotype correlation for GJB2 (connexin 26) deafness", J Med Genet 2004, 41, pp. 147-154.

Diamond et al., Ginkgo biloba extract: mechanisms and clinical indications. Arch. Phys. Med. Rehabil. 81, 2000, pp. 668-678.

Didier et al., "Effects of Ginkgo biloba extract (EGb 761) on cochlear vasculature in the guinea pig: morphometric measurements and laser Doppler flowmetry", Eur. Arch. Otorhinolaryngol. 253, 1996, pp. 25-30.

Duan et al., "Dose and time-dependent protection of the antioxidant N-L-acetylcysteine against impulse noise trauma", Hear. Res. 192, 2004 pp. 1-9.

Eliseev et al., "Bcl-2 and tBid proteins counter-regulate mitochondrial potassium transport", Biochimica et Biophysica Acta 1604, 2003, pp. 1-5.

Evans et al., "Free radicals and hearing. Cause, consequence, and criteria", Ann. N. Y. Acad. Sci. 884, 1999, pp. 19-40.

Fetoni et al., Alpha-Tocopherol protective effects on gentamicin ototoxicity: an experimental study. Int J Audiol 43, 2004, pp. 166-171.

Abstract of Fetoni et al., "Protective Effects of x-Tocopherol Against Gentamicin-induced Oto-vestibula Toxicity: An Experimental Study", Acta Otolaryngol, 2003, No. 123, 1 page.

Fischer et al., "Protection of the Cochlea by Ascorbic Acid in Noise Trauma", HNO 57(4), Apr. 2009, pp. 339-344 and English language abstract for Fischer et al., "Protection of the Cochlea by Ascorbic Acid in Noise Trauma", HNO 57(4), Apr. 2009, pp. 339-344.

Floyd, "Antioxidants, oxidative stress, and degenerative neurological disorders", Proc Soc Exp Biol Med 222, 1999, pp. 236-245.

Forge et al., "Aminoglycoside Antibiotics", Audiol Neurootol 5, 2000, pp. 3-22.

Garetz et al., "Sulphydryl compounds and antioxidants inhibit cytotoxicity to outer hair cells of a gentamicin metabolite in vitro", Hear Res 77, 1994, pp. 75-80.

Godar et al., "Spectral Dependence of UV-Induced Immediate and Delayed Apoptosis: The Role of Membrane and DNA Damage", Photochemistry and Photobiology, vol. 62, No. 1, 1995, pp. 108-113.

Godar, "UVA1 Radiation Triggers Two Different Final Apoptotic Pathways", The Society for Investigative Dermatology Inc., 1999, pp. 3-12.

Gordin et al., Magnesium: a new therapy for idiopathic sudden sensorineural hearing loss. Otol. Neurotol. 23, 2002, pp. 447-451.

Green et al., "Audiological Manifestations and Features of Connexin 26 Deafness", Aud Med. 2003,1, pp. 5-11.

Green et al., "Genetic testing to identify deaf newborns", JAMA. 284, 2000, p. 1245.

Green et al., "Presentation, Hearing Improvement on A CEMg in a Child with Connexin 26 Hearing Loss", Feb. 2011 (University of Michigan, University of Florida), 5 pages.

Gunther et al., "Biochemical mechanisms affecting susceptibility to noise-induced hearing loss", Am. J. Otol. 10, 1989, pp. 36-41.

Gutteridge et al., "Antioxidant protection and oxygen radical signaling. In: Gilbert, D.L., Colton, C.A., (Eds.), Reactive oxygen (56) References Cited

OTHER PUBLICATIONS species in biological systems: An interdisciplinary approach", Kluwer Academic/Plenum Publishers, New York. 1999, pp. 189-218.

Halliwell, "Free Radicals in Biology and Medicine", 3rd Ed., Oxford Univ. Press (1999), Chapter 3—Antioxidant defences, pp. 105-245.

Haupt et al., Preventive magnesium supplement protects the inner ear against noise-induced impairment of blood flow and oxygenation in the guinea pig. Magnes. Res. 15, 2002, pp. 17-25.

Haupt et al., "Therapeutic efficacy of magnesium in acoustic trauma in the guinea pig", Orl. J. Otorhinolaryngol. Relat. Spec. 65, 2003, pp. 134-139.

Heinrich et al, "Ascorbic Acid Reduces Noise-Induced Nitric Oxide Production in the Guinea Pig Ear", Laryngoscope 118, The American Laryngological, Rhinological and Otological Society, Inc., May 2008, pp. 837-842.

Henderson et al., The role of antioxidants in protection from impulse noise. Ann. N. Y. Acad. Sci. 884, 1999, pp. 368-380.

Hight et al., "Noise-induced hearing loss in chinchillas pre-treated with glutathione monoethylester and R-PIA", Hear. Res. 179, 2003, pp. 21-32.

Hilgert et al., "Forty-six genes causing nonsyndomic hearing impairment: Which ones should be analyzed in DNA diagnostics?", Mutation Research 681, 2009, pp. 189-196.

Hilgert et al., "Phenotypic variability of patients homozygous for the GJB2 mutation 35delG cannot be explained by the influence of one major modifier gene", European Journal of Human Genetics, 2009, 17, pp. 517-524.

Hoffman et al., "Potentiation of ototoxicity by glutathione depletion", Ann Ototol Rhinol Laryngol 97, 1, 1988, pp. 36-41.

Hou et al., "Effects of alpha-tocopherol on noise-induced hearing loss in guinea pigs", Hear. Res. 179, 2003, pp. 1-8.

Hu et al., "R-phenylisopropyladenosine attenuates noise-induced hearing loss in the chinchilla". Hear. Res. 113, 1997, pp. 198-206.

Inoue et al., "ATP-sensitive K+ channel in the mitochondrial inner membrane", Letters to Nature, vol. 352, Jul. 18, 1991, pp. 244-247.

Ising et al., "Increased noise trauma in guinea pigs through magnesium deficiency", Arch. Otorhinolaryngol. 236, 1982, pp. 139-146.

Jackson et al., "Antioxidant strategies for post-noise hearing loss recovery, International Symposium—Pharmacologic Strategies for Prevention and Treatment of Hearing Loss and Tinnitus", Niagra Falls, Ottawa, Canada, 2005, 1 page.

Jacono et al., "Changes in cochlear antioxidant enzyme activity after sound conditioning and noise exposure in the chinchilla", Hear Res 117, 1998, pp. 31-38.

Joachims et al., "Antioxidants in treatment of idiopathic sudden hearing loss", Otol. Neurotol. 24, 2003, pp. 572-575.

Joachims et al., "Dependence of noise-induced hearing loss upon perilymph magnesium concentration", J. Acoust. Soc. Am. 74, 1983, pp. 104-108.

Joachims et al., "Oral magnesium supplementation as prophylaxis for noise-induced hearing loss: results of a double blind field study", Schriftenr. Ver. Wasser. Boden. Lufthyg. 88, 1993, pp. 511-516.

Jung et al., "Effects of Ginkgo biloba extract on the cochlear damage induced by local gentamicin installation in guinea pigs", J. Korean Med. Sci. 13, 1998, pp. 525-528.

Kalkanis et al., "Vitamin E reduces cisplatin ototoxicity", Laryngoscope 114, 2004, pp. 538-542.

Kelsell et al., "Connexin 26 mutations in hereditary non-syndromic sensorineural deafness", Letters to Nature, vol. 387, May 1997, pp. 80-83.

Kenna et al., "Audiologic phenotype and progression in GJB2 (Connexin 26) hearing loss", Arch Otolaryngol Head Neck Surg. 36(1), 2010, pp. 81-87.

Kikuchi et al., "Gap junction systems in the mammalian cochlea", Brain Research Reviews 32, 2000, pp. 163-166.

Knight, "Popping pill may prevent hearing loss", [Online] http://www.newscientist.com/article.ns?id=dn2666 (posted Aug. 13, 2002; verified Feb. 25, 2005), 2 pages.

Kopke et al., "A radical demise—Toxins and trauma share common pathways in hair cell death", Ann N Y Acad Sci 884, 1999, pp. 171-191.

Kopke et al., "Candidate's thesis: Enhancing intrinsic cochlear stress defenses to reduce noise-induced hearing loss", Laryngoscope 112, 2002, pp. 1515-1532.

Kopke, "NAC for Noise: From the bench top to the clinic," International Symposium—Pharmacologic Strategies for Prevention and Treatment of Hearing Loss and Tinnitus, Niagra Falls, Ottawa, Canada, 2005, 1 page.

Kopke et al., "Reduction of noise-induced hearing loss using L-NAC and salicylate in the chinchilla", Hear. Res. 149, 2000, pp. 138-146.

Kujawa et al., "Acceleration of Age-Related Hearing Loss by Early Noise Exposure: Evidence of a Misspent Youth," Journal of Neuro., Feb. 15, 2006, 26(7), pp. 2115-2123.

Kujawa, "Adding insult to injury: Noise-induced and age-related hearing loss interactions," International Symposium—Pharmacologic Strategies for Prevention and Treatment of Hearing Loss and Tinnitus, Niagra Falls, Ottawa, Canada, 2005, 1 page.

Kulawiak et al., "BK channel openers inhibit ROS production of isolated rat brain mitochondria", Experimental Neurology 212, 2008, pp. 543-547.

Kwon et al., "Sodium salicylate inhibits expression of COX-2 through suppression of ERK and subsequent NF-kappaB activation in rat ventricular cardiomyocytes", Arch Pharm Res 26, 2003, pp. 545-553.

Laurikainen et al., "Betahistine Effects on Cochlear Blood Flow: From the Laboratory to the Clinic", Acta Otolaryngol, Supp. 544, 2000, pp. 5-7.

Laurikainen et al., "Non-Specific Effect of Beettahistine on Cochlear Electrophysiology in Guinea Pig", Acta Otolayngol (Stockh), Supp. 529, 1997, pp. 77-79.

Abstract of Laurikainen et al., "The Vascular Mechanism of Action of Betahistine in the Inner Ear of the Guinea Pig", Eur Arch Otorhinolaryngol, 1998, No. 255, 1 page.

Lautermann et al., "Glutathione protection against gentamicin ototoxicity depends on nutritional status", Hear Res 86, 1995, pp. 15-24.

Le Prell et al., "Electromotile hearing: Acoustic tones mask psychophysical response to high-frequency electrical stimulation of intact guinea pig cochlea", J, Acoust. Soc. Am. 120 (6), Dec. 2006, pp. 3889-3900.

Le Prell et al., "Free Radical Scavengers Vitamins A, C and E Plus Magnesium Reduce Noise Trauma", Free Radical Biology & Medicine 42, 2007, pp. 1454-1463.

Le Prell et al., "Mechanisms of Noise-Induced Hearing Loss Indicate Multiple Methods of Prevention", Hearing Research 226, Elsevier B.V., 2007, pp. 22-43.

Le Prell et al., Pathways for protection from noise induced hearing loss, Noise Health 5, 2003, pp. 1-17.

Li et al., "Salicylate protects hearing and kidney function from cisplatin toxicity without compromising its oncolytic action",Lab Invest 82, 2002, pp. 585-596.

Lohle, "The influence of a chronic vitamin A deficiency on the acoustic sensory cells and the ganglion spirale cochleae of the rat", An electron microscope study. Arch. Otorhinolaryngol. 229, 1980, pp. 45-53.

Lohle, "Ultrastructural changes in the organ of Corti and in the ganglion spiral cochleae after vitamin A deficiency", Pathol. Res. Pract. 179, 1985, pp. 560-567.

Lopez-Gonzalez et al., "Ototoxicity caused by cisplatin is ameliorated by melatonin and other antioxidants", J. Pineal Res. 28, 2000, pp. 73-80.

Martinez et al., "Gap-Junction Channel Dysfunction in Deafness and Hearing Loss," Antioxidants & Redox Signaling, vol. 11, No. 2, 2009, pp. 309-372.

McFadden et al., Dietary Vitamin C Supplementation Reduces Noise-Induced Hearing Loss in Guinea Pigs, Hearing Research 202, 2005, pp. 200-208.

(56) References Cited

OTHER PUBLICATIONS

Abstract of McFadden et al., "M40403, a superoxide dismutase minetic, protects cochlear hair cells from gentamicin, but not cisplatin toxicity", Science Direct, Toxicology and Applied Pharmacology, 2003, No. 186, 1 page.
Miller et al., "Interactive Effects of Aging with Noise Induced Hearing Loss", Scand. Audiol, 27, 1998, pp. 53-61.
Miller et al., "Mechanisms and Prevention of Noise-Induced Hearling Loss", Otol Jpn, 16(2), 2006, p. 139.
Miller et al., "8-iso-prostaglandin F(2alpha), a product of noise exposure, reduces inner ear blood flow", Audiol. Neurootol. 8, 2003, pp. 207-221.
Minami et al., "Creatine and Tempol Attenuate Noise-Induced Hearing Loss", Brain Res. May 7, 2007, pp. 1-13.
Morton et al., "Newborn Hearing Screening—A Silent Revolution", New Engl J Med 354, 2006, pp. 2151-2164.
Nageris et al. "Magnesium treatment for sudden hearing loss", Ann. Otol. Rhinol. Laryngol. 113, 2004, pp. 672-675.
Nickel et al., "Gap junctions and connexins in the inner ear: their roles in homeostasis and deafness", Current Opinion in Otolryngology & head and Neck Surgery 16, 2008, pp. 452-457.
Niki, "Action of ascorbic acid as a scavenger of active and stable oxygen radicals", Am J Clin Nutr 54, 1991, pp. 1119S-1124S.
Niki et al., "Interaction among Vitamin C, Vitamin E, and Beta-Carotene ^ 1-3", Am J Clin Nutr 62(suppl), 1995, pp. 1322S-1326S.
Niki, "Interaction of Ascorbate and Alpha-Tocohpperol", Department of Reaction Chemistry, Faculty of Engineering, University of Tokyo, pp. 186-199.
Niki, "Lipid antioxidants: How they may act in biological systems", Br. J. Cancer (1987), 55, Suppl. VIII, pp. 153-157.
Ohinata et al., "Glutathione limits noise-induced hearing loss", Hearing Research 146, 2000, pp. 28-34.
Ohinata, "Intense noise induces formation of vasoactive lipid peroxidation products in the cochlea", Brain Res. 878, 2000, pp. 163-173.
Ohinata et al., "Protection from noise-induced lipid peroxidation and hair cell loss in the cochlea", Brain Res. 966, 2003, pp. 265-273.
Ohlemiller et al., "Early Elevation of Cochlear Reactive Oxygen Species following Noise Exposure", Audiol Neurootol 4, 1999, pp. 229-236.
Oleinick et al., "The Photobiology of Photodynamic Therapy: Cellular Targets and Mechanisms", Radiation Research 150 (Suppl.), 1998, pp. S146-S156.
Omenn et al., "Effects of a combination of beta carotene and vitamin A on lung cancer and cardiovascular disease", N. Engl. J. Med. 334, 1996, pp. 1150-1155.
Perlman et al., "Cochlear blood flow and acoustic trauma", Acta Otolaryngol. (Stockh). 54, 1962, pp. 99-119.
Pierson et al., "Prophylaxis of kanamycin-induced ototoxicity by a radioprotectant", Hear Res 4, 1981, pp. 79-87.
Piwonska et al., "Differential Distribution of Ca 2+-Activated Potassium Channel Beta 4 Subunit in Rat Brain: Immunolocalization in Neuronal Mitochondria", Neuroscience 153, 2008, pp. 446-460.
Priuska et al., "Formation of free radicals by gentamicin and iron and evidence for an iron-gentamicin complex", Biochem Pharmacol 50(11), 1995, pp. 1749-1752.
Rabinowitz et al., "Antioxidant status and hearing function in noise-exposed workers", Hear. Res. 173, 2002, pp. 164-171.
Romeo, "The Therapeutic Effect of Vitamins A and E in Neurosensory Hearing Loss", [Italian] Journal Article—Acta Vitamininol. Enzymol. 7 Suppl, 1985, pp. 85-92, 1 Page English Abstract from OVID Search Results.
Rybak et al., "Ototoxicity", Kidney International 72, 2007, pp. 931-935.
Ryter et al., "Comprehensive Invited Review: Mechanisms of Cell Death in Oxidative Stress", Antioxidants & Redox Signaling, vol. 9, No. 1, 2007, pp. 49-89.

Schact, "Antioxidant therapy attenuates aminoglycoside-induced hearing loss", Ann. N. Y. Acad. Sci. 884, 1999, pp. 125-130.
Schafer et al., "Comparing Beta-Carotene, Vitamin E and Nitric Oxide as Membrane Antioxidants", Biol. Chem. vol. 383, Mar./Apr. 2002, pp. 671-681.
Scheibe et al. "Preventive effect of magnesium supplement on noise-induced hearing loss in the guinea pig", Eur. Arch. Otorhinolaryngol. 257, 2000, pp. 10-16.
Scheibe et al., "Preventive magnesium supplement reduces ischemia-induced hearing loss and blood viscosity in the guinea pig", Eur Arch Otorhinolaryngol 257, 2000, pp. 355-361.
Scheibe et al. "Therapeutic effect of parenteral magnesium on noise-induced hearing loss in the guinea pig", Magnes. Res. 15, 2002, pp. 27-36.
Scheibe et al., "Total magnesium concentrations of perilymph, cerebrospinal fluid and blood in guinea pigs fed different magnesium-containing diets", Eur. Arch. Otorhinolaryngol. 256, 1999, pp. 215-219.
Schneider et al., "Gingko biloba (Rokan) therapy in tinnitus patients and measurable interactions between tinnitus and vestibular disturbances", Int. Tinnitus. J. 6, 2000, pp. 56-62.
Seidman, "Effects of dietary restriction and antioxidants on presbyacusis", Laryngoscope 110, 2000, pp. 27-38.
Seidman et al., "Effects of resveratrol on acoustic trauma", Otolaryngol. Head Neck Surg. 129, 2002, pp. 463-470.
Sergi et al., "The role of antioxidants in protection from ototoxic drugs", Acta Otolaryngol. Suppl. (Stockh), 2004, pp. 42-45.
Sha et al., "Aspirin to prevent gentamicin-induced hearing loss", N Engl J Med 354(17), 2006, pp. 1856-1857.
Sha et al., "Formation of reactive oxygen species following bioactivation of gentamicin", Free Rad Biol Med 26(3-4), 1999, pp. 341-347.
Sha et al., "Salicylate attenuates gentamicin-induced ototoxicity", Lab Invest 79, pp. 807-813.
Shoji et al., "Differential Protective Effects of Neurotrophins in the Attenuation of Noise-Induced Hair Cell Loss", Hearing Research 146, 2000, pp. 134-142.
Siemen et al., "Ca 2+-Activated K Channel of the BK-Type in the Inner Mitochondrial Membrane of a Human Glioma Cell Line", Biochemical and Biophysical Research Communications, 257, 1999, pp. 549-554.
Song et al.,"Iron chelators protect from aminoglycosideinduced cochleo- and vestibulotoxicity in guinea pig", Free Radic. Biol. Med. 25, 1998, pp. 189-195.
Song et al., "Variable efficacy of radical scavengers and iron chelators to attenuate gentamicin ototoxicity in guinea pig in vivo", Hear Res 94, 1996, pp. 87-93.
Soares et al., "Sequestering Ability of Butylated Hydroxytoluene, Propyl Gallate, Resveratrol, and Vitamins C and E against ABTS, DPPH, and Hydroxul Free Radicals in Chemical and Biological Systems", J. Agric. Food Chem. 51, 2003, pp. 1077-1080.
Szabo et al., "A Novel Potassium Channel in Lymphocyte Mitochondria", The Journal of Biological Chemistry, vol. 280, No. 13, Apr. 1, 2005, pp. 12790-12798.
Takemura et al., "Direct Inner Ear Infusion of Dexamethasone Attenuates Noise-Induced Trauma in Guinea Pig", Hearing Research 196, 2004, pp. 58-68.
Takumida et al., "Radical scavengers for Meniere's disease after failure of conventional therapy: a pilot study", Acta Otolaryngol. (Stockh). 123, 2003, pp. 697-703.
Tanswell et al., "Antioxidant therapy in critical care medicine", New Horizons 3, 1995, pp. 330-341, 1 page abstract from OVID:Search Results on Apr. 22, 2006.
Teranishi et al., "Effects of alpha-tocopherol on cisplatin-induced ototoxicity in guinea pigs", Hear. Res. 151, 2011, pp. 61-70.
Tsuchihashi et al., "Action of Beta-Carotene as an Antioxidant against Lipid Peroxidation", Archives of Biochemistry and Biophysics, vol. 323, No. 1, Oct. 20, 1995, pp. 137-147.
Usami et al., "Differential cellular distribution of glutathione—an endogenous antioxidant—in the guinea pig inner ear", Brain Res. 743, 1996, pp. 337-340.

(56) References Cited

OTHER PUBLICATIONS

Wang et al., "Bcl-XL disrupts death-inducing signal complex formation in plasma membrane induced by hypoxia/reoxygenation", The FASEB Journal, Research Communication, pp. 1826-1833.
Wang et al., "Hepatocyte Growth Factor Protects against Hypoxia/Reoxygenation-induced Apoptosis in Endothelial Cells", The Journal of Biological Chemistry, vol. 279, No. 7, Feb. 13, 2004, pp. 5237-5243.
Wang et al., "Tanshinone (Salviae miltiorrhizae Extract) Preparations Attenuate Aminoglycoside-Induced Free Radical Formation in Vitro and Ototoxicity In Vivo", Antimicrobial Agents and Chemotherapy, Jun. 2003, vol. 47, No. 6, pp. 1836-1841.
Wangemann, "K+ Cycling and Its Regulation in the Cochlea and the Vestibular Labyrinth", Audiol Neurootol 7, 2002, pp. 199-205.
Wangemann, "K+ Cycling and the endocochlear potential", Hearing Research 165, 2002, pp. 1-9.
Watanabe et al., "Acoustic stimulation promotes the expression of inducible nitric oxide synthase in the vestibule of guinea pigs", Acta Otolaryngol. Suppl. 553: (Stockh)., 2004, pp. 54-57.
Weijl et al., "Supplementation with antioxidant micronutrients and chemotherapy-induced toxicity in cancer patients treated with cisplatin-based chemotherapy: a randomised, double-blind, placebo-controlled study", Eur. J. Cancer 40, 2004, pp. 1713-1723.
Yamashita, et al., "Delayed production of free radicals following noise exposure", Brain Res 1019, 2004, pp. 201-209.
Yamashita et al., "Post-exposure treatment attenuates noise-induced hearing loss", Neuroscience, 134, 2005, pp. 633-642.
Yamasoba et al., "Attenuation of Cochlear Damage From Noise Trauma by an Iron Chelator, a Free Radical Scavenger and Glial Cell Line-Derived Neurotrophic Factor in Vivo", Brain Research 815, 1999, pp. 317-325.
Yamasoba et al., "Role of glutathione in protection against noise-induced hearing loss", Brain Res. 784, 1998, pp. 82-90.
Yamasoba et al., "Influence of intense sound exposure on glutathione synthesis in the cochlea", Brain Research 804, 1998, pp. 72-78.
Yamasoba, T., "Oxidative Stress in Applied Basic Research and Clinical Practice, Oxidative Stress and Age-Related Hearing Loss, Part VI—Interventions to Prevent Age-Related Hearing Loss", Free Radicals in ENT Pathology, Eds.: Miller, J., Le Press, C and Rybak, L., Humana Press, 2015, pp. 335-349.
Yu, "Regulation and critical role of potassium homeostasis in apoptosis", Progress in Neurobiology 70, 2003, pp. 363-386.
Zhao et la., "Oxidative damage pathways in relation to normal tissue injury", The British Journal of Radiology, 80, 2007, pp. S23-S31.
International Search Report, International Application No. PCT/US 07/01422, dated Mar. 4, 2008, 2 pages.
The Alpha-Tocopherol, Beta Carotene Cancer Prevention Study Group. The effect of vitamin E and beta carotene on the incidence of lung cancer and other cancers in male smokers. N. Engl. J. Med. 330, 1994, pp. 1029-1035.
Constricted Blood Vessels, downloaded from http://www.menieres.org/forums/NonCGI/Forum1/HTML/003686.html, 1 page.
"A Randomized, Placebo-Controlled, Clinical Trial of High-Dose Supplementation With Vitamins C and E, Beta Carotene and Zinc for Age-Related Degeneration and Vision Loss", Arch Ophthalmol, 119(10), Oct. 2001, pp. 1417-1436.
Agrawal, Y., et al., "Prevalence of Hearing Loss and Differences by Demographic Characteristics Among U.S. Adults", Data from the National Health and Nutrition Examination Survey, 1999-2004. Arch Intern Med. 2008; 168, pp. 1522-1530.
Labdiet, "PicoLab Laboratory Rodent Diet", Jan. 9, 2014, 1 page.
Population Reference Bureau, "Human Population: Urbanization, Largest Urban Agglomerations, 1975, 2000, 2025, Teachers Guide: Discussion Guide", originally downloaded from http://www.prb.org/Publications/Less-Plans/HumanPopulation/Urbanization.aspx on Aug. 27, 2016.
World Health Organization, "Hearing Loss Due to Recreational Exposure to Loud Sounds: A Review", 2015, pp. 1-32.
World Health Organization, "WHO Global Estimates on Prevalence of Hearing Loss—Mortality and Burden of Diseases and Prevention of Blindness and Deafness", 2012, 15 pages.
Utility U.S. Appl. No. 15/272,973, filed Sep. 22, 2016.

METHOD FOR TREATING AGE-RELATED HEARING LOSS (ARHL)

RELATED APPLICATIONS

This patent application is a continuation-in-part of U.S. patent application Ser. No. 14/847,178 filed on Sep. 8, 2015. U.S. patent application Ser. No. 14/847,178 is a continuation-in-part of U.S. patent application Ser. No. 13/839,760 filed on Mar. 15, 2013, which is now U.S. Pat. No. 9,144,565. U.S. patent application Ser. No. 13/839,760 is a continuation-in-part of U.S. patent application Ser. No. 13/679,224 filed on Nov. 16, 2012, which is now U.S. Pat. No. 8,927,528. U.S. patent application Ser. No. 13/679,224 is a continuation-in-part of U.S. patent application Ser. No. 12/761,121 filed on Apr. 15, 2010, which is now U.S. Pat. No. 8,338,397. U.S. patent application Ser. No. 12/761,121 is a continuation-in-part of U.S. patent application Ser. No. 11/623,888 filed on Jan. 17, 2007, which is now U.S. Pat. No. 7,951,845. U.S. patent application Ser. No. 11/623,888 claims priority to and all advantages of U.S. Provisional Patent Application No. 60/760,055, filed on Jan. 19, 2006. U.S. patent application Ser. No. 13/679,224 is also a continuation-in-part of U.S. patent application Ser. No. 13/091,931 filed on Apr. 21, 2011, which is now U.S. Pat. No. 8,338,398. U.S. patent application Ser. No. 13/091,931 is a continuation of U.S. patent application Ser. No. 11/623,888 filed on Jan. 17, 2007, which is now U.S. Pat. No. 7,951,845. U.S. patent application Ser. No. 11/623,888 claims priority to and all advantages of U.S. Provisional Patent App. Ser. No. 60/760,055, filed on Jan. 19, 2006.

GOVERNMENT LICENSE RIGHTS

This invention was made with Government support under DC004058 awarded by the National Institutes of Health. The Government has certain rights in this invention.

BACKGROUND OF THE DISCLOSURE

Field of the Disclosure

The present disclosure generally relates to method for treating age-related hearing loss (ARHL) including administering a composition to a mammal, wherein the composition consists essentially of a biologically effective amount of vitamin A, vitamin E, vitamin C, a vasodilator comprising magnesium, and, optionally, a withanolide, and/or resveratrol.

Description of the Related Art

Extensive studies have been performed on compositions for treating various types of hearing loss/damage. ARHL, or presbycusis, typically begins when the person is in his/her mid to late 50s. ARHL affects approximately 50% of the population of people in their 60s, and approximately three-fourths of the population of people in their mid-70s. Because the ageing population is growing rapidly, the prevalence of hearing loss is growing in the general population, with concomitant decrease in quality of life, including loss of communication, reduced social interaction and a significant increase in the health care economic burden. Moreover hearing impairment has recently been associated with increased cognitive dysfunction in the elderly, contributing to prevalence of Alzheimer's and dementia.

Presbycusis (or ARHL) typically expresses itself as a loss in sensitivity to high frequency sounds, described as sensory presbycusis. However, presbycusis may take other forms, such as a low frequency hearing loss or a flat hearing loss affecting all frequencies of hearing. Each of these hearing losses have been identified with different pathological changes occurring over time in different structures of the inner ear, including sensory presbycusis, neural presbycusis, and strial or metabolic presbycusis.

ARHL typically occurs slowly over time, and can be identified by default without a known cause. However, some risk factors have been identified as contributing to ARHL including, but not limited to, malnutrition, cardiovascular disease, diabetes, smoking, exposure to heavy metals, and exposure to noise. Exposure to noise also contributes to about 25 to 50% of the burden of ARHL. Said differently, noise exposure enhances ARHL, where about 25 to 50% of people with ARHL have a history of exposure to high levels of noise. Urban environments are increasingly noisy, and there is a rapidly increasing percentage of the world's population living in urban environments. For example, in the year 1800, about three percent of the world's population lived in urban environments. By the year 1900, almost fourteen percent of the world's population lived in urban environments. By the year 1950, about thirty percent of the world's population lived in urban environments. In 2008, the world's population was about evenly split between urban and rural areas, with more than four hundred cities with over one million people and nineteen cities with over ten million people. In addition, in 2008, about seventy-four percent of the population lived in urban environments in more developed countries, while forty-four percent of the population lived in urban environments in less developed countries. However, urbanization is occurring rapidly in many less developed countries, and about seventy percent of the world's population should be living in urban environments by the year 2050 with most of this urban growth occurring in the less developed countries.

In addition to increasing environmental and industrial noises, high levels of noise exposure from rapid adoption of digital music technologies and personal listening devices places about 1.1 billion people worldwide at risk for early onset of hearing loss.

Intense noise is an environmental stress factor for the ear that may cause damage to the ear, which may lead to cell death. For instance, intense noise can cause damage to micromechanical properties of sensory transducers in the ear, changes in blood flow in the ear, modification in intracellular ion transport properties, depletion of sensory cell transmitter substances (e.g. glutamate), changes in post synaptic membrane transmitter receptors (e.g. gluR) on afferent nerve fibers, modification of dispersion and uptake properties of transmitters in extracellular, synaptic spaces, and/or changes in postsynaptic membrane biophysical properties that may affect space- and time-constant properties modifying depolarization. Intense noise can also cause changes of an excitotoxic nature in postsynaptic membranes, causing destruction of afferent neural tissues. Any one or more of these changes may result in modification of spontaneous activity in individual or small populations of afferent nerve fibers, which can result in a change in the sensitivity of hearing and/or the perception of tinnitus.

Additionally, intense noise (i.e., high noise levels sufficient to cause hearing loss) demands greater activity of the respiratory chain to create adenosine triphosphate (ATP), resulting in excess free radical formation. Typically, in the normal ear under normal stress, the endogenous antioxidant systems are sufficient to maintain normal homeostatic function of the inner ear. However, under high levels of stress, increased free radical formation may contribute to excitotoxicity and can damage the DNA. Through the process of lipid peroxidation, the increased free radical formation can destroy inner and extracellular membranes that can lead to temporary loss in hearing sensitivity, distortions of sounds, muffling of sounds, and permanent hearing loss associated with cell death. While a number of factors may influence these changes, intercellular redox properties of cells and blood flow to the inner ear may be of particular importance in causing these changes. Stress induced hearing loss becomes evermore prevalent in the ageing inner ear with reduced blood flow and reduced efficiency of antioxidant systems.

Dietary supplements including *ginkgo biloba*, melatonin, zinc, lipoflavenoids, and vitamin supplements are available for treating hearing loss; however, no evidence is available that any of these supplements are actually beneficial for ARHL or tinnitus. In addition, no chemical treatments have been attempted to prevent repeated exposure to high noise levels leading to ARHL. Accordingly, there remains an opportunity to develop an effective composition and method for treating age-related hearing loss (ARHL).

SUMMARY OF THE DISCLOSURE

The subject disclosure provides a method for treating age-related hearing loss (ARHL) that includes the step administering a composition to a mammal, wherein the composition consists essentially of a biologically effective amount of vitamin A, vitamin E, vitamin C, a vasodilator comprising magnesium, and, optionally, a withanolide, and/or resveratrol.

As shown below, each of the pathological changes, or downregulation in function, in the structures of the inner hear have in common a basic age-related underlying mechanism—an age-related reduction in blood flow to the inner ear and an age-related reduction in endogenous antioxidant systems that prevent formation and elimination of free radicals. The composition of the present disclosure is a unique micronutrient formulation for treating ARHL including an agent that increases inner ear blood flow and agents that supplement antioxidant properties of the inner ear.

Reduction in blood flow occurs in many tissues of the body with aging, including the ear. With reduction in blood flow, there is typically a lack of oxygenation of the tissue and an accumulation of waste products, particularly when the tissue is under stress. As described below, various factors contribute to reduction in cochlear blood flow, and a particular agent that can block these blood flow reductions and increase blood flow to the inner ear. In addition, free radicals in the inner ear is an important factor in hearing loss, indicating that reduction in cochlear blood flow may also be beneficial for the treatment of ARHL. The examples set forth below show a reduction in antioxidant efficiency, and demonstrates how this reduction can lead to cell pathology and death. The examples also show that the unique formulation of antioxidants of the composition of the present disclosure can prevent this pathology. Accordingly, the composition and method of the present disclosure can be used to effectively treat and/or prevent ARHL.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

A composition for treating ARHL includes components that may function through different biological mechanisms to provide an additive effect that is equal to or greater than a sum of the effect of the individual components. The composition is typically used for treating ARHL that may result from age-related stress to an inner ear of a mammal or may have no known cause. The stress may be further defined as mechanically-induced metabolic trauma, mechanical/metabolic trauma, stress trauma, stress-induced damage, or environmental stress. It may also reflect a downregulation of inner ear blood flow and endogenous antioxidant systems that occur gradually with aging that increases the sensitivity of the inner ear to pathology that would be well below a threshold for damage to a younger ear. However, it is also possible that the composition may also be used to treat or prevent all types of ARHL, including, sensory presbycusis, neural presbycusis, and strial and metabolic presbycusis.

A method in accordance with the instant disclosure includes the step of administering a composition to a mammal that includes components that function through different biological mechanisms. In the method, the composition is typically used for preventing and treating ARHL, and thereby preserving hearing in the ear of the mammal.

In various embodiments, the trauma may be further defined as stress over time to the inner ear, where stress is defined as environmental or endogenous actions that demand relatively high level of energy production by the cells of the inner ear. Intense noise can cause damage to micromechanical properties of sensory transducers in the ear, changes in blood flow in the ear, modification in intracellular ion transport properties, depletion of sensory cell transmitter substances (e.g. glutamate), changes in post synaptic membrane transmitter receptors (e.g. gluR) on afferent nerve fibers, modification of dispersion and uptake properties of transmitters in extracellular, synaptic spaces, and/or changes in postsynaptic membrane biophysical properties that may affect space- and time-constant properties modifying depolarization. In addition, Intense noise can cause changes of an excitotoxic nature in postsynaptic membranes causing destruction of afferent neural tissues. Any one of these changes can result in modification of spontaneous and evoked activity in small or large populations of afferent nerve fibers, which can result in temporary loss of hearing sensitivity, distortion of sound, or permanent loss of hearing. While a number of factors may influence these changes, intercellular redox properties of cells, blood flow to the inner ear and calcium uptake by postsynaptic afferent nerve fiber membranes may be of particular importance in causing these changes.

The baseline physiological function of systems that underlie normal homeostasis sets the conditions upon which stress agents may effect the inner ear. In a young inner ear, blood flow is resilient and endogenous antioxidant systems are typically robust (except in certain hereditary hearing losses). With age, these systems may be compromised with age itself being a stress factor of the inner ear. One result of noise, age, and/or drug stressors on the inner ear is the formation of excess free radicals in association with the induced metabolic trauma. The free radicals typically damage sensitive structures, such as hair cells within the ear and can initiate processes that can lead to hearing loss. Vasoconstriction may also occur as a result of the noise, which can lead to decreased blood flow to the inner ear and cause cell death that results in NIHL and associated tinnitus. It has been found that the underlying cause of vasoconstriction is noise-induced free radical formation. Specifically, one of the molecules formed in the inner ear as a result of the presence of free radicals is 8-isoprostane-2F alpha, which is a bioactive agent. The bioactive agent induces a constriction of blood vessels in the inner ear, which causes a reduction in blood flow. In order to counteract the free radical formation and the vasoconstriction, the composition of the subject disclosure typically includes at least one scavenger of singlet oxygen, a donor antioxidant, a third antioxidant, and a vasodilator. Unexpectedly, it was found that the composition including the at least one scavenger of singlet oxygen, the donor antioxidant, the third antioxidant, and the vasodilator produce an additive effect that is not only greater than the effect of any one of those components alone, but at least equal to or greater than a sum of the effects of each of the components.

Many genetic hearing disorders are dependent upon a defect in a single gene leading to hearing impairment or deafness, and many reflect defects in more that one gene, and may be associated with other, non hearing, clinical disorder. Early onset of presbycusis may be associated with either class of genetic hearing disorders and thus associated with one (non-syndromic) mutation or with mutations in more than one gene (e.g. syndromic) and may be associated with other inherited clinical disorders.

ARHL may reflect a defect in a gene resulting in flawed gene copies, which mis-instructs production of a protein important for homeostasis and transduction processes in the inner ear. This may lead to antioxidant systems that are less effective in reducing the formation and removal of free radicals in the inner ear tissues. In knock-out animals, this has been shown to lead to early presbycusis. This could also lead to disruption of micromechanical properties of hair cells, depolarization defects, inadequate production and or assembly of transmitter substances, and/or compromised synaptic activity. This may also result in disruption of ion metabolism, e.g. potassium, their distribution and movement in the inner ear and particularly in the lateral wall and sensory cells, and a disruption of cellular homeostasis in these cells, frequently leading to cell death.

Since potassium homeostasis in the inner ear is important for normal function of the sensory cells of the inner ear (hair cells), any disruption tends to result in hearing impairment and may induce hearing loss or tinnitus. Knock-out mouse models of genetic hearing impairment may show early widespread degeneration of both inner and outer hair cells, presumably secondary to defects that upregulate apoptotic cell death pathways. In humans, hearing impairment may begin sometime following birth and progress until profound deafness occurs. However, gene defects may be expressed as mild to moderate hearing impairment.

More specifically, one or more genetic defects may lead to disruption of potassium homeostasis in an inner ear of a mammal. Potassium homeostasis may regulate apoptosis such that stress-driven disruption of inner ear potassium homeostasis may lead to increase production of free radicals by mitochondria directly leading to upregulation of apoptotic cell death pathways, as well as supports direct potassium-induced cytochrome c release and apoptosis. Potassium channels Kv1.3, mitochondrial $Ca^{2+}$ regulated potassium channel, mitoBKCa, and mitochondrial ATP-regulated potassium channel—mitoKATP have been demonstrated in mitochondrial membranes. Mitochondrial potassium channels effect energy production by the mitochondrion. In addition, there may be a direct dependence of free radical formation on potassium channel function during the respiratory chain in mitochondrial function. Moreover, increased mitochondrial K+ influx may result in release of cytochrome c and caspase-3 followed by apoptosis. These events could be blocked by bcl-2, which upregulated the mitochondrial K/H-exchanger, leading to increased removal of $K^+$. In addition, Bcl-2 and tBid proteins may counter-regulate mitochondrial potassium transport. By removing/eliminating excess free radicals antioxidants may restore mitochondrial function. Antioxidants act through a variety of mechanisms. The at least one scavenger of singlet oxygen and the donor antioxidant are two different classes of antioxidants that act through different mechanisms. The third antioxidant, while typically a scavenger of singlet oxygen, may be a different antioxidant that acts through a different mechanism. Scavengers of singlet oxygen reduce free radicals that contribute to inner ear pathology and thus to hearing loss and/or tinnitus. These free radicals may also cause side effects of antibiotic treatment such as kidney damage and loss of balance. More specifically, by reducing free radicals, the scavengers of singlet oxygen prevent, among other damaging effects, the singlet oxygen from reacting with lipids to form lipid hydroperoxides. Lipid hydroperoxides may play a role in causing ARHL.

Even within the class of scavengers of singlet oxygen, it is believed that various antioxidants react at different sites within the body, and in particular, within cells to attenuate free radical formation. For example, one of the scavengers of singlet oxygen is typically vitamin A. In various non-limiting embodiments described herein, the terminology Vitamin A and beta-carotene may be used interchangeably. However, these embodiments in no way limit this disclosure. Vitamin A is a generic term that captures a number of molecules with a biological activity of retinol or carotenoids. Primary dietary forms of vitamin A/retinol include retinol esters and beta-carotene. The beta-carotene is made up of a polyene chain of 11 conjugated double bonds with methyl branches spaced along the polyene chain, capped at both ends by cyclohexenyl rings with 1,1,5-trimethyl substitution. Other forms of vitamin A include xanxthophylls, astaxanthin, canthxanxin, lutein, and zeaxanthin, which include a backbone of beta-carotene with hydroxyl and/or carbonyl substitution on one or more of the cyclohexenyl rings. For purposes of the subject disclosure, the vitamin A is typically present as beta-carotene. Beta-carotene is a powerful scavenger of singlet oxygen, as well as nitric oxide and peroxynitrite, and may also scavenge lipid peroxyl radicals within a lipophilic compartment of a mitochondrial membrane. Beta-carotene is an excellent scavenger of free radicals under normal physiological conditions present in most tissues.

In addition to vitamin A, other scavengers of singlet oxygen may also be present in the composition of the subject disclosure. For example, another scavenger of singlet oxygen that may be present is resveratrol. Resveratrol is more efficient at scavenging hydroxyl radicals than vitamin C, and the addition of resveratrol to the vitamins A may have additive effects.

The at least one scavenger of singlet oxygen may be present in the composition in a biologically effective amount. For purposes of the subject disclosure, the biologically effective amount may be further defined as an amount that is sufficient to produce an additive effect in a reduction in stress induced threshold shift or tinnitus when used in combination with other antioxidants and the magnesium. Additive effect, as used herein, refers to an effect that is equal to or greater than a sum of the effects of the individual components. In order to produce additive effect and the reduction in threshold shift or tinnitus, the at least one scavenger of singlet oxygen is typically present in the composition in a total amount of at least 830 international units (IU), more typically from 830 to 120,000 IU, most typically from about 2,100 to 70,000 IU for an adult dosage.

The amount of the vitamin A present in the composition is dependent upon the form of vitamin A that is used. For example, in one embodiment, vitamin A is present as retinol in an amount of at least 830 IU, more typically from 830 to 10,000 IU, more typically from 2,100 to 10,000 IU, most typically from 2,100 to 8,000 IU. As known in the art, a conversion of IU to weight for vitamin A (as retinol) is 3.33 IU/µg. Thus, at least 830 international units (IU) of vitamin A (as retinol) is equivalent to at least 0.25 mg of vitamin A, from 830 to 10,000 IU of vitamin A (as retinol) is equivalent to from 0.25 to 3 mg of vitamin A, and from 2,100 to 8,000 IU of vitamin A (as retinol) is equivalent to from 0.63 to 2.4 mg vitamin A.

Alternatively, the vitamin A may be present in the composition as beta-carotene, as opposed to retinol. The retinol activity equivalents (RAE) for retinol conversion to beta-carotene, which is a pro-vitamin A carotenoid, is 1 mg to 12 mg. In terms of conversion of the amounts set forth above for the vitamin A present in the composition as retinol to the vitamin A present in the composition as beta-carotene, in one example, a total amount of at least 3.0 mg or at least 830 international units (IU) of vitamin A as beta-carotene, more typically from 3.0 to 180 mg or 830 to 50,000 IU vitamin A as beta-carotene, most typically from about 7.2 to 108 mg or 2000 to 30,000 IU of vitamin A as beta-carotene is typically present for an adult dosage. In another example, a total amount of at least 3.0 mg or at least 10,000 international units (IU) of vitamin A as beta-carotene, more typically from 3.0 to 36 mg or 10,000 to 120,000 IU vitamin A as beta-carotene, most typically from about 7.5 to 21 mg or 25,000 to 70,000 IU of vitamin A as beta-carotene is typically present for an adult dosage.

Specific amounts of the vitamin A present in the composition may be dependent on the body weight of the mammal. In one specific example, the amount of vitamin A present as retinol in the composition is about 0.0178 mg/kg body weight. Thus, for an average human weighing about 70 kg, the amount of vitamin A present as retinol in the composition may be about 1.25 mg. If the vitamin A is in the form of beta-carotene, in one example, the beta carotene in the composition is about 0.257 mg/kg body weight may be present in an amount of about 18 mg. In another example, the beta-carotene in the composition may be about in an amount of about 15 mg.

It is to be appreciated that, when additional scavengers of singlet oxygen such as resveratrol are present in the composition in addition to vitamin A, the total amount of scavengers of singlet oxygen may be greater than the ranges set forth above for the at least one scavenger of singlet oxygen, so long as at least one scavenger of singlet oxygen is present in the amounts set forth above. In addition, other scavengers of singlet oxygen may be used in place of vitamin A, so long as the amount of the at least one scavenger of singlet oxygen is present within the amounts set forth above. When present, the resveratrol is typically included in the composition in an amount of at least 1 mg, more typically in an amount of from 10 mg to 1500 mg, most typically in an amount of from 15 mg to 1000 mg.

Whereas the at least one scavenger of singlet oxygen tends to prevent the initial formation of lipid peroxides, the donor antioxidant tends to reduce peroxyl radicals and inhibits propagation of lipid peroxidation that contributes to inner ear pathology and ARHL. More specifically, the donor antioxidant reacts with and reduces peroxyl radicals and thus serves a chain-breaking function to inhibit propagation of lipid peroxidation. As is evident from the chain-breaking function of the donor antioxidant in lipid peroxidation, the donor antioxidant functions within cell membranes. A specific donor antioxidant that is contemplated for use in the composition of the subject disclosure is vitamin E. Vitamin E is a generic term for all tocols and tocotrienol derivatives with a biological activity of alpha-tocopherol. Primary dietary forms of vitamin E include vitamin E itself and alpha-tocopherol. Trolox®, a water-soluble analogue of alpha-tocopheral commercially available from Hoffman-Laroche, Ltd. of Basel, Switzerland, is a research agent that is typically used as a source of vitamin E.

The donor antioxidant is typically present in the composition, for example, in an amount of at least 75 IU, more typically from 75 IU to 2,000 IU, more typically from 150 to 1,500 IU, most typically from 150 IU to 800 IU. In another example, the donor antioxidant is present in the composition in an amount of at least 75 IU, more typically from 75 IU to 1,500 IU, most typically from 150 IU to 800 IU. As known in the art, a conversion of IU to weight for synthetic vitamin E is 0.66 mg/IU and for natural vitamin E is 0.45 mg/IU. Thus, when the donor antioxidant is synthetic vitamin E, in on example, at least 75 IU of vitamin E is equivalent to at least 50 mg of vitamin E, from 75 to 2,000 IU of synthetic vitamin E is equivalent to from 50 to 1,320 mg of vitamin E, from 150 to 1,500 IU of synthetic vitamin E is equivalent to from 100 to 1,000 mg of vitamin E, and from 150 to 800 IU of synthetic vitamin E is equivalent to from 100 to 536 mg of vitamin E. In another example, when the donor antioxidant is vitamin E, at least 75 IU of vitamin E is equivalent to at least 50 mg of vitamin E, from 75 to 1500 IU of vitamin E is equivalent to from 50 to 1000 mg of vitamin E, and from 150 to 800 IU of vitamin E is equivalent to from 150 to 600 mg of vitamin E. As with the amount and type of vitamin A, specific amounts of the vitamin E present in the composition may be dependent on the body weight of the mammal. In one specific example, the amount of synthetic vitamin E present in the composition is about 3.8 mg/kg body weight. Thus, for an average human weighing about 70 kg, the amount of vitamin E present in the composition may be about 266 mg. In another specific example, the amount of synthetic or natural vitamin E present in the composition is about 2.6 mg/kg body weight. Thus, for an average human weighing about 70 kg, the amount of vitamin E present in the composition may be about 182 mg.

In addition to the at least one scavenger of singlet oxygen and the donor antioxidant, the composition further includes the third antioxidant. While the third antioxidant may be a scavenger of singlet oxygen, the third antioxidant may also be an antioxidant that functions through a different mechanism. When the third antioxidant is a scavenger of singlet oxygen, the at least one scavenger of singlet oxygen is still present in the composition as a separate component from the third antioxidant, and is still present in the composition in the amounts set forth above for the at least one scavenger of singlet oxygen. As a result of the third antioxidant being another scavenger of singlet oxygen, the resulting composition would have at least two scavengers of singlet oxygen.

The third antioxidant is typically vitamin C, which is a scavenger of singlet oxygen and reactive nitrogen species. It is to be appreciated that, although the third antioxidant is typically vitamin C, other antioxidants may be used in place of the vitamin C, and the other antioxidants may function through different mechanisms than vitamin C. The term vitamin C applies to substances that possess antiscorbutic activity and includes two compounds and their salts: L-ascorbic acid (commonly called ascorbic acid) and L-dehydroascorbic acid. In addition to being known as ascorbic acid and L-ascorbic acid, vitamin C is also known as 2,3-didehydro-L-threo-hexano-1, 4-lactone, 3-oxo-L-gulo-furanolactone, L-threo-hex-2-enonic acid gamma-lactone, L-3-keto-threo-hexuronic acid lactone, L-xylo-ascorbic acid and antiscorbutic vitamin. Vitamin C is known to scavenge both reactive oxygen species and reactive nitrogen species. It can be oxidized by most reactive oxygen and nitrogen species, including superoxide, hydroxyl, peroxyl and nitroxide radicals, as well as such non-radical reactive species as singlet oxygen, peroxynitrite and hypochlorite. Vitamin C thus inhibits lipid peroxidation, oxidative DNA damage, and oxidative protein damage.

In contrast to vitamin A, which functions best under conditions present in most tissues, water-soluble vitamin C is an excellent free radical scavenger in an aqueous phase to thus reduce free radicals at a site different from that of vitamin A. More specifically, ascorbic acid functions to reduce free radicals in fluid, such as in cytoplasmic fluid and/or blood, before the free radicals reach cell membranes.

The third antioxidant is typically present, for example, in an amount of at least 4,000 IU, more typically from 4,000 to 60,000, more typically from 8,000 to 40,000 IU, most typically from 8,000 to 20,000 IU. In another example, the third antioxidant is typically present in an amount of at least 4,000 IU, more typically from 6,000 to 40,000 IU, and most typically from 8,000 to 20,000 IU. Using vitamin C as an example for converting IU to weight units for the third antioxidant, as known in the art, a conversion of IU to weight for vitamin C is 0.05 mg/IU. Thus, at least 4,000 IU of vitamin C is equivalent to at least 200 mg of vitamin C, from 6,000 to 60,000 IU of vitamin C is equivalent to from 300 to 3,000 mg vitamin C, from 6,000 to 40,000 IU of vitamin C is equivalent to from 300 to 2,000 mg, from 8,000 to 40,000 IU of vitamin C is equivalent to from 400 to 2,000 mg vitamin C, and from 8,000 to 20,000 IU vitamin C is equivalent to from 400 to 1,000 mg vitamin C. As with vitamins A and E, specific amounts of the vitamin C or other third antioxidant present in the composition may be dependent on the body weight of the mammal. In one specific example, the amount of vitamin C present in the composition is about 7.14 mg/kg body weight. Thus, for an average human weighing about 70 kg, the amount of vitamin C present in the composition may be about 500 mg.

As set forth above, the composition further includes a vasodilator. Typically, the vasodilator includes magnesium; however, the vasodilator, for purposes of the subject disclosure, may include other vasodilators in place of or in addition to magnesium, in place of or in addition to those including magnesium, or may include only magnesium or only magnesium-containing compounds. Vasodilators can be used for treating ARHL. Vasodilators including magnesium prevent decreases in cochlear blood flow and oxygenation via biochemical mechanisms involving changes in calcium concentration and prostaglandins. Deficient cochlear blood flow and lack of oxygenation can contribute to ARHL by causing metabolic changes in lateral wall tissues important for maintaining normal homeostasis of the inner ear, e.g. endocochlear potential, and normal transduction; and may cause cell death in sensitive hair cells within a cochlea of the ear. Vasodilators including magnesium have also been found to improve the efficacy of immunosuppressant therapy or carbogen inhalation therapy in recovery from sudden hearing loss and/or tinnitus. Furthermore, it has been found that magnesium deficiency leads to increased calcium channel permeability and greater influx of calcium into cochlear hair cells and afferent nerve endings, increased glutamate release, and auditory nerve excitotoxicity, each of which play a role in health of the inner ear.

Vasodilators have been suggested for the treatment of ARHL. When the ear is under oxidative stress, the vasodilator magnesium exhibits an unexpected additive effect when combined with the biologically effective amounts of at least one scavenger of singlet oxygen, the donor antioxidant, and the third antioxidant, especially when at least one scavenger of singlet oxygen is vitamin A, the donor antioxidant is vitamin E, and the third antioxidant is vitamin C. The additive effect referred to above is greater than not only the most efficacious of the components for treating inner ear pathology that causes ARHL, NIHL, and tinnitus, but also typically greater than the sum of the effects of each of the components. While vasodilators other than those including magnesium are envisioned for purposes of the present disclosure, additive effects are not observed with all vasodilators. For example, betahistine, which is another known vasodilator, does not exhibit an additive effect.

The vasodilator including magnesium typically includes a magnesium salt or magnesium salt complex and, more specifically, magnesium sulfate or magnesium citrate. Other vasodilators including magnesium that may be suitable for purposes of the subject disclosure include; magnesium acetate, magnesium aspartate, magnesium carbonate, magnesium chloride, magnesium fumarate, magnesium gluconate, magnesium glycinate, magnesium hydroxide, magnesium lactate, magnesium oxide, magnesium salicylate, magnesium stearate, and magnesium sulfate. Other representative salts include but are not limited to; hydrobromide, hydrochloride, bisulfate, nitrate, arginate, ascorbate, oxalate, valerate, oleate, palmitate, laurate, borate, benzoate, phosphate, tosylate, maleate, fumarate, succinate, taurate, tartrate, naphthylate, mesylate, glucoheptonate, lactobionate and laurylsulphonate salts.

Typically, the vasodilator is present in the composition in an amount of at least 50 mg. For example, when the vasodilator is magnesium, the magnesium is typically present in an amount of from 50 to 450 mg, most typically from 100 to 350 mg. As with vitamins A, C, and E, specific amounts of the vasodilator present in the composition may be dependent on the body weight of the mammal. In one specific example, the amount of the vasodilator including magnesium present in the composition is about 4.46 mg/kg body weight. Thus, for an average human weighing about 70 kg, the amount of the vasodilator including magnesium present in the composition may be about 312 mg. In another example, the amount of the vasodilator including magnesium present in the composition is about 2.14 mg/kg body weight. Thus, for an average human weighing about 70 kg, the amount of the vasodilator including magnesium present in the composition may be about 150 mg.

Non-limiting examples of amounts of the typical components included in the composition, along with more and most typical amounts, are summarized in Table 1 below.

TABLE 1

| Component | | Amount | More Typical Amount | Most Typical Amount | Typical Dosage, mg/kg body weight |
|---|---|---|---|---|---|
| Vitamin A | | ≥830 IU | 830-10,000 IU | 2100-8,000 IU | 0.0178 mg/kg |
| | Vitamin A As beta-carotene | ≥830 IU | 830-50,000 IU | 2,000-30,000 IU | 0.257 mg/kg |
| Vitamin C | | ≥4,000 IU | 4,000-60,000 IU | 8,000-20,000 IU | 7.14 mg/kg |
| Vitamin E | | ≥75 IU | 75-2000 IU | 150-800 IU | 3.8 mg/kg (synthetic) |
| Magnesium | | ≥50 mg | 50-450 mg | 100-350 mg | 4.46 mg/kg |

With respect to Table 1, the amounts specified for the antioxidants and the vasodilator correlate, in terms of biological effectiveness, to amounts used for humans. Furthermore, it is to be appreciated that the biologically effective amounts of the antioxidants and vasodilator may be lower within the above ranges for children than for the average human, based on lower US recommended daily allowances and maximum intake levels for children. This is evident based on the typical dosages in Table 1 based on mg/kg.

Other non-limiting examples of amounts of the typical components included in the composition, along with more and most typical amounts, are summarized in Table 2 below.

TABLE 2

| Component | | Amount | More Typical Amount | Most Typical Amount | Typical Dosage, mg/kg body weight |
|---|---|---|---|---|---|
| Vitamin A | | ≥830 IU | 830-120,000 IU | 2,100-70,000 IU | — |
| | Vitamin A As Retinol | ≥830 IU | 830-50,000 IU | 2,100-5,900 IU | 0.0178 mg/kg |
| | Vitamin A As beta-carotene | ≥10,000 IU | 10,000-120,000 IU | 25,000-70,000 IU | 0.214 mg/kg |
| Vitamin C | | ≥4,000 IU | 6,000-40,000 IU | 8,000-20,000 IU | 7.14 mg/kg |
| Vitamin E | | ≥75 IU | 75-1,500 IU | 150-800 IU | 2.6 mg/kg |
| Magnesium | | ≥50 mg | 50-450 mg | 100-350 mg | 2.14 mg/kg |

With respect to Table 2, the amounts specified for the antioxidants and the vasodilator correlate, in terms of biological effectiveness, to amounts used in animal studies on guinea pigs. Furthermore, it is to be appreciated that the biologically effective amounts of the antioxidants and vasodilator may be lower within the above ranges for children than for the average human, based on lower U.S. recommended daily allowances and maximum intake levels for children. This is evident based on the typical dosages in Table 2 based on mg/kg.

In addition to the antioxidants and vasodilator, other components may also be present in the composition for treating ARHL. These components may be used for treating the side effects of the antibiotic treatment also. For example, in one embodiment, the composition further includes a withanolide. Withanolides have been suggested for use in anti-inflammatory, anti-tumor, cytotoxic, and immunological applications. One example of a specific withanolide that may be included in the composition of the subject disclosure is the withanolide extracted from day lily plants. The extract is a powerful natural antioxidant which may be effective in preventing cell death in the inner ear by interrupting the cell-death pathway initiated by deafferentation of the auditory nerve. When included in the composition, the withanolide may be present in an amount of at least 10 ppm, more typically from 10 to 1000 ppm. Additional components, besides withanolides, can also be included. Typically, the composition is free of components that interfere with the biological mechanisms through which the at least one scavenger of singlet oxygen, the donor antioxidant, the third antioxidant, and the vasodilator function. The composition is also typically free of additional components that could degrade or neutralize the at least one scavenger of singlet oxygen, the donor antioxidant, the third antioxidant, and the vasodilator function when mixed therewith prior to internally administering the composition to the mammal. Those of skill in the art can readily identify such components in view of the mechanisms by which the individual components in the composition function as set forth above (e.g., components that cause vasoconstriction, various oxidizing agents, etc.).

It is also to be appreciated that, even if additional components are present in the composition that could interfere with the mechanisms by which the at least one scavenger of singlet oxygen, the donor antioxidant, the third antioxidant, and the vasodilator function, the composition described above is may still be effective for purposes of treating side effects of the antibiotic treatment. As one example, and as described in further detail below, the composition including the at least one scavenger of singlet oxygen, the donor antioxidant, the third antioxidant, and the vasodilator may be effective for treating hearing loss and/or tinnitus and other side effects of antibiotic treatment when administered in conjunction with aminoglycoside antibiotics. This is true even though aminoglycoside antibiotics, themselves, are responsible for causing hearing loss and add to the burden of ARHL and other side effects such as kidney damage and loss of balance through free radical formation.

In view of the fact that components as detrimental as aminoglycosides can be administered in conjunction with the composition described above, it is clear that additional components that are less detrimental to the specific mechanisms by which the at least one scavenger of singlet oxygen, the donor antioxidant, the third antioxidant, and the vasodilator function can also be present in the composition with an expectation that the composition maintains effectiveness for purposes of treating side effects of other stresses that may contribute to ARHL. Examples of some additional components that may be included in the composition include, but are not limited to, excipients, flavoring agents, fillers, binders, and additional vitamins or minerals not specifically mentioned herein.

As alluded to above, the method for treating ARHL and the method for treating side effects of other stressors to the inner ear the instant disclosure includes the step of internally administering the composition of the subject disclosure to a mammal. The composition may be orally administered to the mammal, such as in the form of a tablet, liquid, gel, etc. Alternatively, the composition may be intravenously administered to the mammal through an IV or an injection of the composition and may also be locally administered via the round window membrane of the cochlea. As a specific example, the vitamins A, C, and E, the vasodilator including magnesium, and the optional components may be first combined to form the composition, with the composition then administered to the mammal. Alternatively, the vitamins A, C, and E, the vasodilator including magnesium, and the other optional components may be separately administered, in which case the composition forms within the mammal.

For purposes of the subject disclosure, ARHL is typically associated with stress (noise, antibiotic, genetic)-induced hearing loss as objectively measured in terms of differences in threshold shift, or through measurement of a percentage of hair cell loss. In guinea pig studies, ARHL is objectively measured as a change in hearing threshold measured behaviorally, or more commonly as a change in the threshold of the Auditory Brainstem Response (ABR). This is clearly demonstrated in a consistent and reliable manner after application of stress agents such as noise and drugs and observed in ARHL.

For purposes of the subject disclosure, ARHL may be objectively measured in terms of differences in threshold shift, or through measurement of a percentage of hair cell loss. In guinea pig studies, ARHL and the efficacy of the composition for treating ARHL may be measured as differences in threshold shift from baseline threshold sensitivity at 0.5, 1, 2, 4, 8, and 16 kHz, measured in an aging ear as compared to an untreated control measured at the same age. Larger differences in threshold shift correlate to less ARHL and greater efficacy of the composition for treating the antibiotic-induced tinnitus.

It is has been shown that hair cell loss correlates to threshold shift. For example, in guinea pig ears that recover from temporary threshold shift, morphological damage is limited to tips of stereocilia in a third row of outer hair cells (OHCs) whereas ears from animals with permanent threshold shift have damage to all three rows of OHCs and, in some cases, the inner hair cells (IHCs), with damage throughout the length of the stereocilia as well as the to the body of the hair cell. Loss of hair cells is the defining characteristic of sensory presbycusis.

Figure 1:
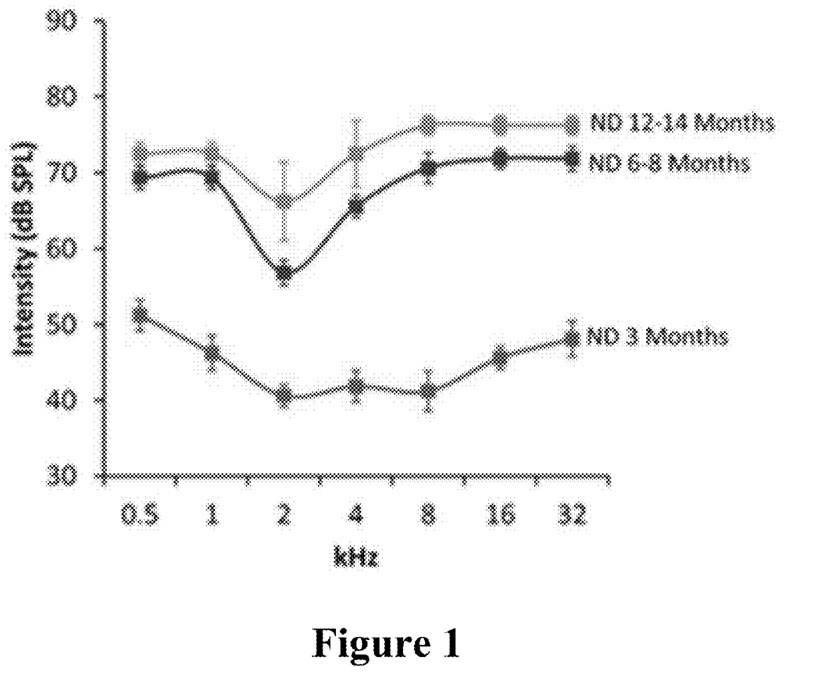
FIGS. 1 and 2 are graphs illustrating the auditory brainstem response (ABR) thresholds for mammals 3 months of age, mammals 6-8 months of age, and mammals 12-14 months of age. Mammals on a normal diet are designated ND (FIG. 1), and mammals on the enriched ACEMg (Soundbites) diet are designated ED (FIG. 2).
Figure 2:
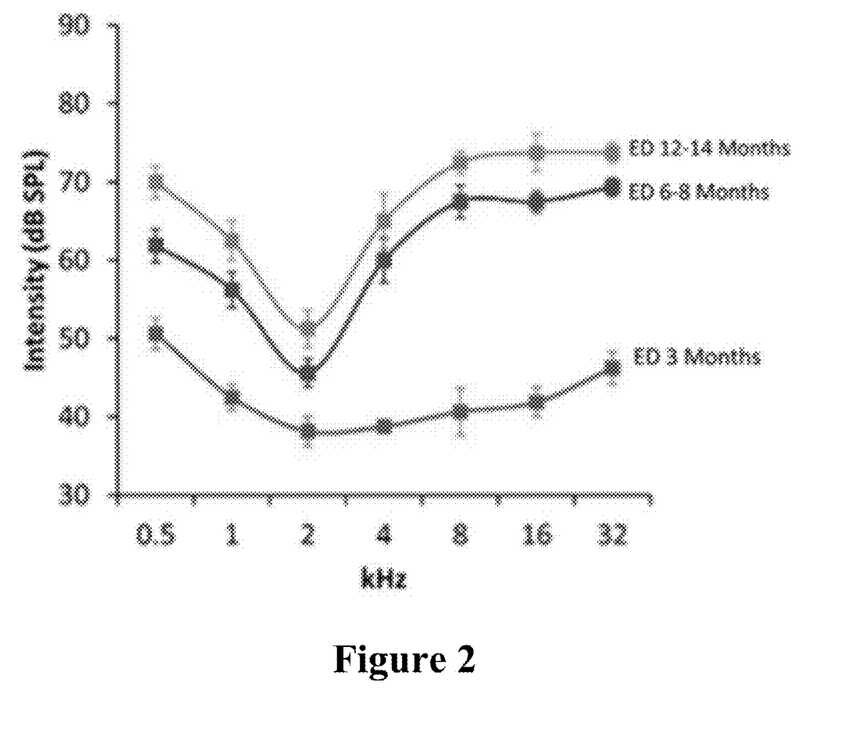
Figure 3:
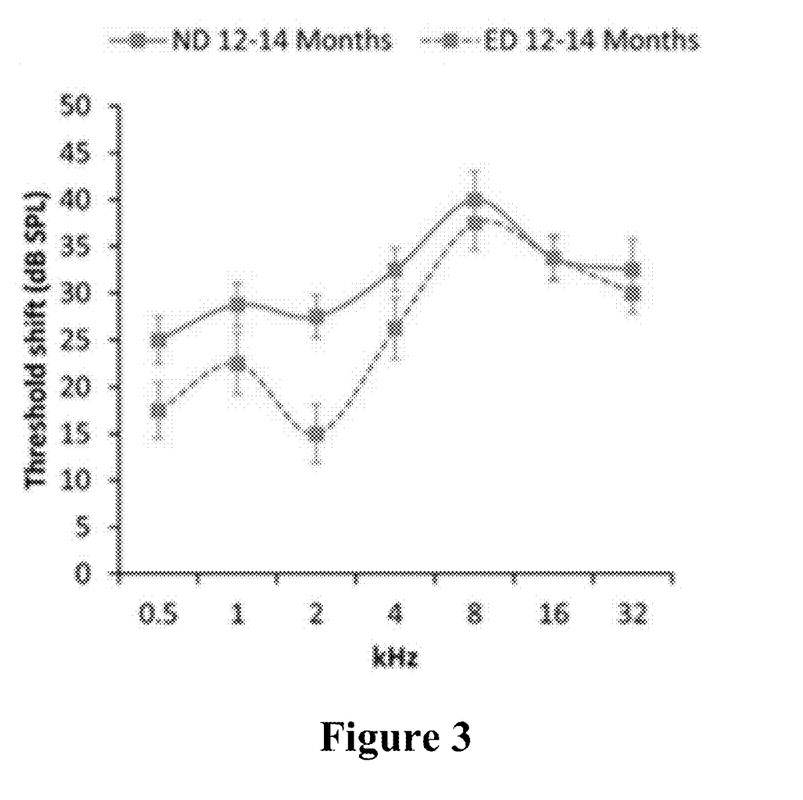
FIG. 3 is a graph illustrating a difference in threshold elevations (shifts) in mammals from a 3-month old baseline to 12-14 months of age.

In one example, and with reference to FIGS. 1-3, the composition of the present disclosure is administered to three month old mammals starting ten days preceding a moderate level of noise equivalent to a rock concert, for about 1 hr/day for 5 days/week until the mammals were twelve to fourteen months old. For comparison, a similar group of mammals on a normal control (non-supplemented) diet was exposed to a similar noise. The normal or control diet includes carotene, vitamins A, D, and E, ascorbic acid, and magnesium sufficient to maintain a healthy diet in a rat and in amounts which are significantly less than for the supplemented diet. The results shown in FIGS. 1-3 show clear elevations in threshold sensitivity to all frequencies tested over time. The results also show that at twelve to fourteen months of age, there is a significant increase in the auditory thresholds of all mammals as expected at this age. However, the ARHL threshold shifts observed (particularly in the 0.5 to 8 kHz, the speech-related frequencies, range) in the mammals fed the composition of ACEMg is significantly lower than that observed in mammals on the control diet. The efficacy of the supplemented diet is also clearly shown in FIG. 3, comparing age-related threshold shifts in supplemented and non-supplemented diets.

In this example, the component diet was fed to the mammals throughout the study paradigm. The noise level given was significant, but was no greater than that experienced in many occupations and leisure time activities. The mammals were exposed to the noise for about 1 hr/day for 9 to 11 months. Given the duration of daily exposure and the differences in life span, this may equate to less than a decade of the human lifespan and is well below the working life of the average person in a noisy occupation or the period that a person exposes himself/herself to loud levels of music amplified in live performance (such as at a concert), though personal listening devices, or other noise stresses associated with urban recreational, industrial, and/or manufacturing environments.

After initial administration, the composition is typically administered to the mammal each day throughout the study, or for humans, the composition is typically administered to the human throughout life to prevent ARHL. Although excellent results have been achieved through such treatment, it is to be appreciated that other treatment regimens may also prove efficacious for purposes of the present disclosure.

For the method for treating side effects of antibiotic treatment, which contribute to ARHL the composition is internally administered to the mammal in conjunction with administration of the antibiotic. In this regard, the method also includes the step of internally administering the antibiotic, which antibiotic is capable of inducing hearing loss in the mammal. It is to be appreciated that, even though the antibiotic with which the composition is administered is capable of inducing hearing loss, the method of the instant disclosure is not strictly limited to treatment of ARHL that is enhanced by the antibiotics. More specifically, the method of the instant disclosure proscribes the step of administering the subject composition in conjunction with administration of the antibiotic for any purpose including for treating any side effect of the antibiotics including not only antibiotic-induced ARHL, but also kidney damage, loss of balance, among other side effects.

To maximize effectiveness of the treatment described herein, it is desirable to establish stable serum levels of the at least one scavenger of singlet oxygen, the donor antioxidant, the third antioxidant, and the vasodilator at the time that the stress induces increased free radical formation and damage to the inner ear. Typically, the composition is administered to the mammal immediately, which is sufficient to achieve the stable serum levels of the at least one scavenger of singlet oxygen, the donor antioxidant, the third antioxidant, and the vasodilator before the antibiotics begin to materially cause the side effects such as ARHL. In one embodiment, the composition is internally administered prior to administration of the stress.

Once administration of the composition has begun, the composition is typically administered each day during stress administered to maintain adequate serum levels of the at least one scavenger of singlet oxygen, the donor antioxidant, the third antioxidant, and the vasodilator. Additionally, the composition is typically administered for the duration of stress, which with age and a less robust homeostatic system means daily. This is typically performed for purposes of ensuring that adequate serum levels of the at least one scavenger of singlet oxygen, the donor antioxidant, the third antioxidant, and the vasodilator are maintained until the serum levels of the antibiotic decrease, and typically until all of the additional free radicals formed secondary to the stress are eliminated.

In varying embodiments, an average difference in threshold shift in mammals from baseline threshold sensitivity at 2 and 4 kHz, as compared to an untreated control, is improved by at least three fold (10 decibels). To obtain those results, the composition may be orally administered ten days prior to the beginning of the exposure to the noise and administered again each day until the mammals were assessed at 12 to 14 months of age. The threshold shift is measured after exposure to the noise using auditory brainstem response (ABR) testing. Similar results would be anticipated using other alternative measures of auditory or sensory cell function, such as psychophysical tests or otoacoustic emission measures. While effectiveness of treatment in accordance with the method of the instant disclosure is related to measurement and mitigation of shifts in threshold, it is to be appreciated that the method is not strictly limited to treatment of sensory presbycusis alone.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims is herein expressly contemplated. The disclosure is illustrative including words of description rather than of limitation. Many modifications and variations of the present disclosure are possible in light of the above teachings, and the disclosure may be practiced otherwise than as specifically described herein. In additional non-limiting embodiments, all values and ranges of values within any aforementioned range of numbers are hereby expressly contemplated.

What is claimed is:

1. A method for treating age-related hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol.

2. A method as set forth in claim 1 wherein the step of internally administering the composition is further defined as orally administering the composition to the mammal.

3. A method as set forth in claim 1 wherein the step of internally administering the composition is further defined as intravenously administering the composition to the mammal.

4. A method as set forth in claim 1 further comprising the step of detecting tinnitus in a mammal.

5. A method as set forth in claim 1 wherein the vitamin A is present in the composition in an amount of at least 830 IU.

6. A method as set forth in claim 1 wherein the vitamin C is present in the composition in an amount of at least 4,000 IU.

7. A method as set forth in claim 1 wherein the vitamin E is further defined as a water-soluble analogue of alpha-tocopheral.

8. A method as set forth in claim 1 wherein the vitamin E is present in the composition in an amount of at least 75 IU.

9. A method as set forth in claim 1 wherein the vasodilator is present in an amount of at least 50 mg.

10. A method as set forth in claim 1 wherein the composition provides an additive effect that is equal to or greater than a sum of the effects of the individual components.

11. A method for treating age-related hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after peroxyl radical formation.

12. A method as set forth in claim 11 wherein the formation of peroxyl radicals is further defined as oxidative DNA damage.

13. A method as set forth in claim 11 wherein the formation of peroxyl radicals is further defined as oxidative protein damage.

14. A method as set forth in claim 11 wherein the composition provides an additive effect that is equal to or greater than a sum of the effects of the individual components.

15. A method for treating age-related hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after lipid peroxidation in the mammal.

16. A method as set forth in claim 15 wherein the composition provides an additive effect that is equal to or greater than a sum of the effects of the individual components.

17. A method for treating age-related hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after vasoconstriction of blood vessels in an ear of the mammal.

18. A method as set forth in claim 17 wherein the composition provides an additive effect that is equal to or greater than a sum of the effects of the individual components.

19. A method for treating age-related hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after formation of lipid peroxyl radicals within a lipophilic compartment of a mitochondrial membrane in the mammal.

20. A method as set forth in claim 19 wherein the composition provides an additive effect that is equal to or greater than a sum of the effects of the individual components.

\* \* \* \* \*